United States Patent
Tsuji

(10) Patent No.: US 7,046,758 B1
(45) Date of Patent: May 16, 2006

(54) X-RAY CT APPARATUS

(75) Inventor: Masahiro Tsuji, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 291 days.

(21) Appl. No.: 10/130,098

(22) PCT Filed: Nov. 9, 2000

(86) PCT No.: PCT/JP00/07902

§ 371 (c)(1),
(2), (4) Date: Jul. 29, 2002

(87) PCT Pub. No.: WO01/34032

PCT Pub. Date: May 17, 2001

(30) Foreign Application Priority Data

Nov. 10, 1999 (JP) .................................. 11/319818

(51) Int. Cl.
*A61B 6/00* (2006.01)
(52) U.S. Cl. ........................................... 378/15; 378/4
(58) Field of Classification Search ................ 378/15, 378/4, 901, 19
See application file for complete search history.

(56) References Cited

U.S. PATENT DOCUMENTS

| 5,485,493 A | * | 1/1996 | Heuscher et al. | 378/15 |
| 5,864,598 A | * | 1/1999 | Hsieh et al. | 378/4 |
| 5,987,157 A | * | 11/1999 | Schaller et al. | 382/131 |
| 6,028,908 A | * | 2/2000 | Taguchi | 378/15 |
| 6,243,438 B1 | * | 6/2001 | Nahaliel et al. | 378/19 |

FOREIGN PATENT DOCUMENTS

JP          10043174 A    *   2/1998

* cited by examiner

Primary Examiner—David V. Bruce
Assistant Examiner—Hoon Song
(74) Attorney, Agent, or Firm—Antonelli, Terry, Stout and Kraus, LLP.

(57) ABSTRACT

Both an X-ray source and an X-ray detector are moved in a pitch which is smaller than a width of this detector. Since both the X-ray source and the X-ray detector are rotated by an angle of 360° within one move distance, a CT measurement is carried out. An X-ray detection amount of a slice width narrower than an X-ray effective detection width is calculated based upon the X-ray detection amount measured in the above-described manner.

8 Claims, 9 Drawing Sheets

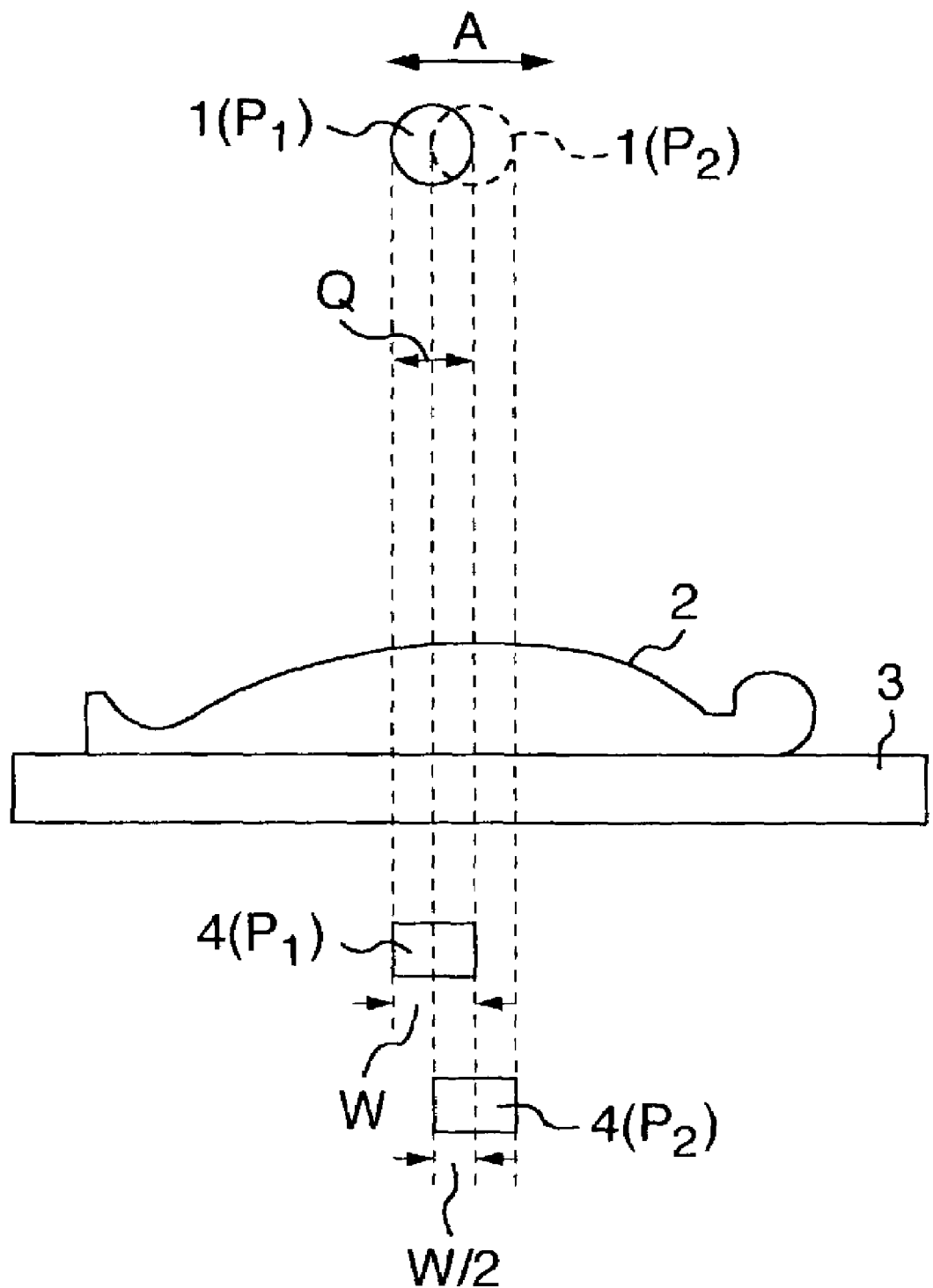

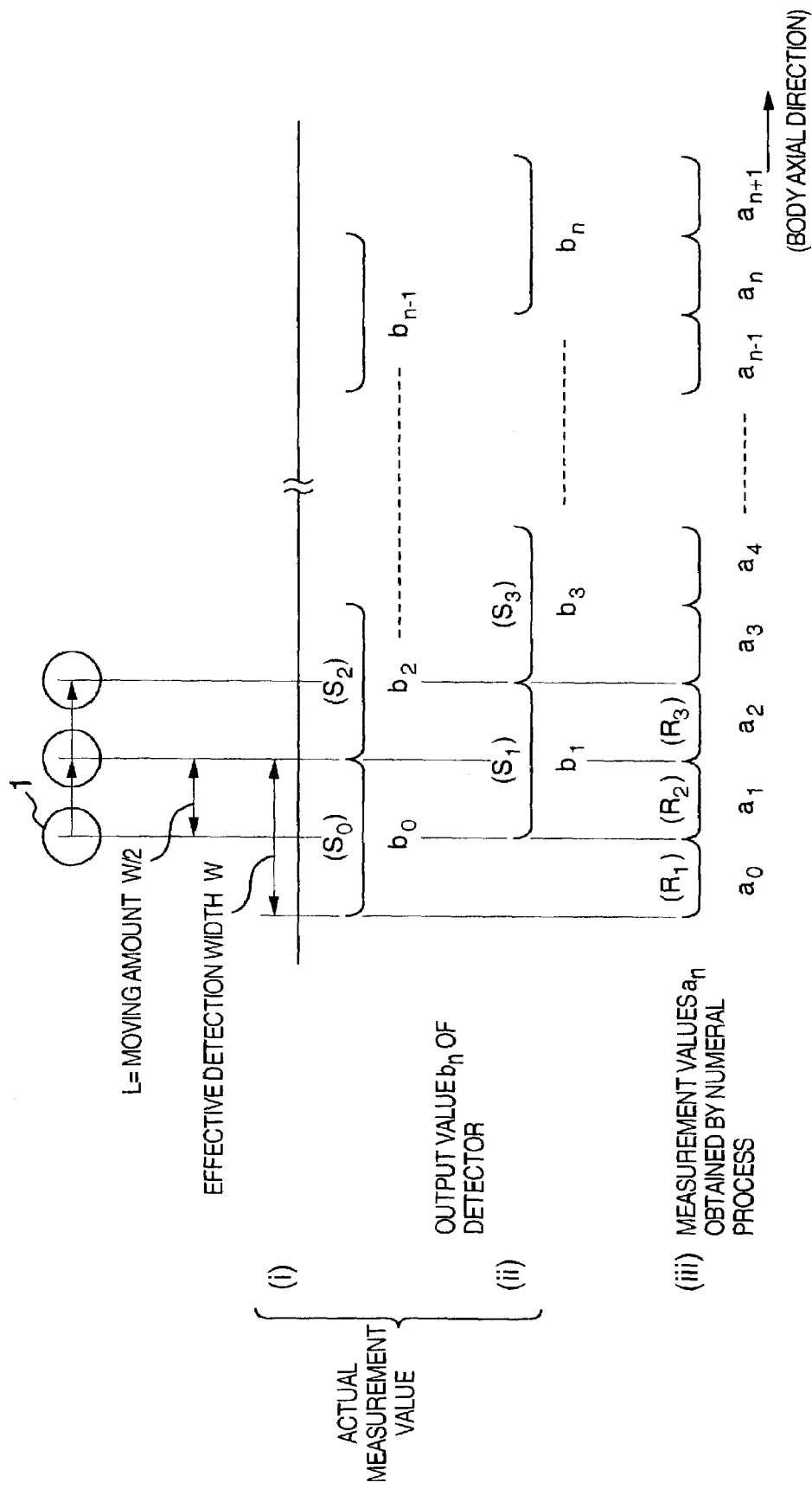

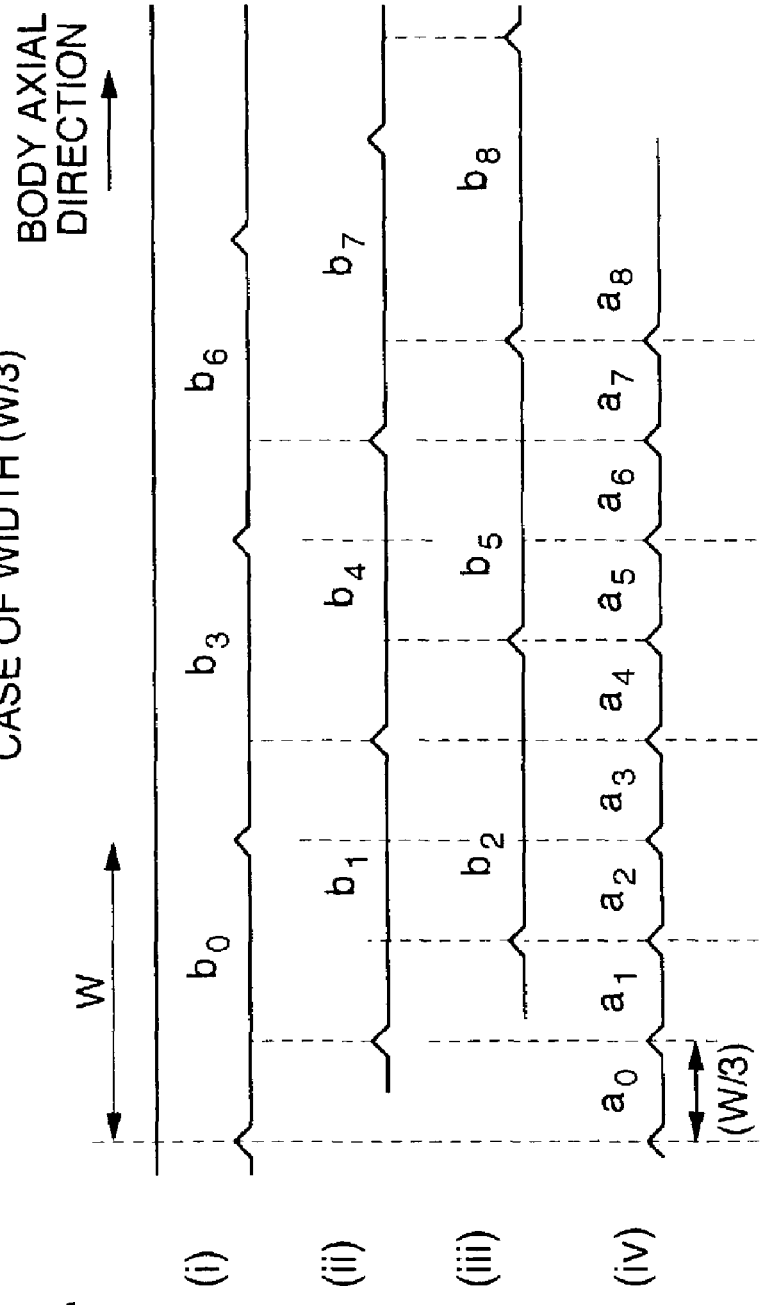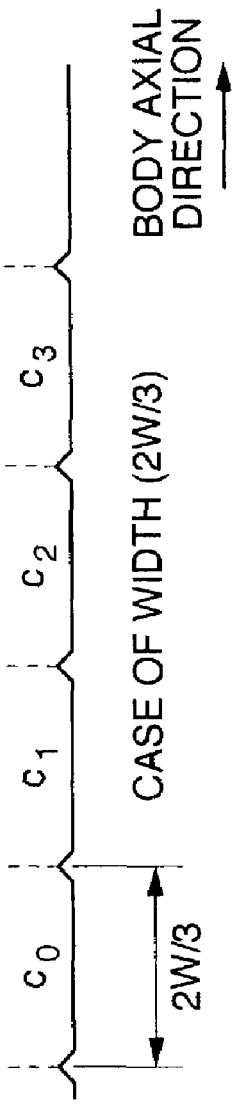
FIG. 4A
FIG. 4B

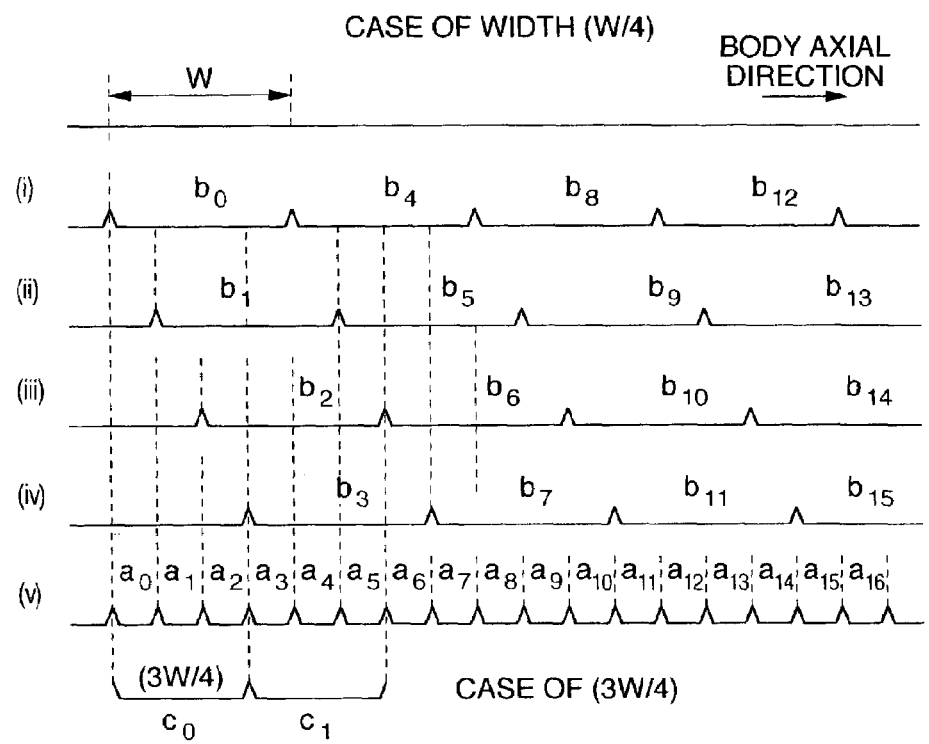
FIG. 5A
FIG. 5B
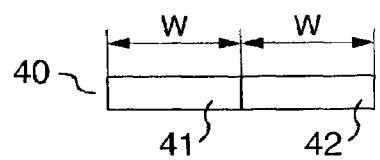
FIG. 6

X-RAY CT APPARATUS

TECHNICAL FIELD

The present invention relates to an X-ray CT apparatus for acquiring tomographic images having variable slice thicknesses.

BACKGROUND ART

In an X-ray CT apparatus, while both an X-ray source and an X-ray detector positioned opposite to the X-ray source are rotated around an object to be examined, X-ray beams (fan beams) are irradiated from the X-ray source in a fan shape, and then, an amount of X-rays which have penetrated through the object is detected by the X-ray detector. Transmission X-ray amount data detected by the X-ray detector is acquired, and a tomographic image is reconstructed based on this acquired data by a reconstructing means.

A fan-shaped X-ray beam owns a certain extended projection angle and a certain width. This width will be referred to as a "beam slice width." Since a width of an X-ray detector is made equal to this beam slice width, a slice width of a tomographic image is made coincident with the beam slice width.

Conventionally, in order to obtain a tomographic image having a slice width which is thinner than a width of an X-ray detector, a slice width adjusting means is employed. As this slice width adjusting means, since a collimator for limiting an irradiation range of X-rays along a thickness direction thereof may be installed, or a mechanism for adjusting a detection range of the X-ray detector along a width direction thereof may be provided, such a method for limiting an X-ray incident plane has been conducted.

As previously described, the conventional method owns such a drawback that the adjusting means should be provided.

DISCLOSURE OF THE INVENTION

The present invention has been made to solve the above-described drawback, and therefore, has an object to provide an X-ray CT apparatus capable of acquiring a tomographic image having a slice width which is thinner than a width of an X-ray incident plane of an X-ray detector.

The present invention discloses an X-ray CT apparatus including:
   an X-ray source for irradiating a fan beam X-ray having a predetermined width;
   an X-ray detector which is arranged opposite to the X-ray source while sandwiching an object under examination, and is rotated around the object to be examined in combination with the X-ray source under opposite-arranging condition;
   means for moving, plural times, any one of both the X-ray source and the X-ray detector located opposite to the X-ray source, and a bed on which the object is mounted at a predetermined pitch which is made narrower than an effective X-ray detection width of the X-ray;
   means for rotating both the X-ray source and the X-ray detector located opposite to the X-ray source at positions before/after the movement, or during the movement so as to perform a CT measurement, and for acquiring a detection signal obtained from the X-ray detector;
   means for obtaining detection data having a slice width from the detection signal, which is larger than the predetermined pitch by integer times; and
   means for reconstructing a tomographic image having a slice width which is narrower than an effective detection width of the X-ray from the detection data.

Furthermore, the present invention discloses an X-ray CT apparatus including:
   an X-ray source for irradiating a fan beam X-ray having a predetermined width;
   a multi-channel X-ray detector which is arranged opposite to the X-ray source while sandwiching an object to be examined, and is rotated around the object in combination with the X-ray source under opposite-arranging condition;
   means for moving, plural times, any one of both the X-ray source and said X-ray detector located opposite to the X-ray source, and a bed on which the object is mounted at a predetermined pitch which is made narrower than an effective X-ray detection width of the X-ray;
   means for rotating both the X-ray source and the X-ray detector located opposite to the X-ray source at positions before/after the movement, or during the movement so as to perform a CT measurement, and for acquiring a detection signal obtained from the X-ray detector;
   means for obtaining detection data having a slice width from detection signal, which is smaller than the predetermined pitch; and
   means for reconstructing a tomographic image having a slice width which is narrower than an effective detection width of the X-ray from the detection data.

In accordance with the present invention, the slice width can be variably changed. Also, since the slice width can be made narrow, body axial resolution can be improved. Furthermore, since the slice width can be variably changed, resolution along the body axial direction can be variably set.

BRIEF DESCRIPTION OF THE DRAWINGS

FIG. 2 is a diagram for explaining changing of a slice width in the present invention.

FIG. 3 is a time chart for acquiring a virtual measurement value "a" in the present invention.

FIG. 4A is a time chart for acquiring a virtual measurement value "a" in the present invention.

FIG. 4B is a time chart for acquiring a virtual measurement value "a" in the present invention.

FIG. 5A is a time chart for acquiring a virtual measurement value "a" in the present invention.

FIG. 5B is a time chart for acquiring a virtual measurement value "a" in the present invention.

FIG. 6 is a diagram for indicating a multi-slice X-ray detector.

BEST MODE FOR CARRYING OUT THE INVENTION

Referring now to the accompanying drawings, preferable embodiment modes of an X-ray CT apparatus according to the present invention will be described.

Figure 1:
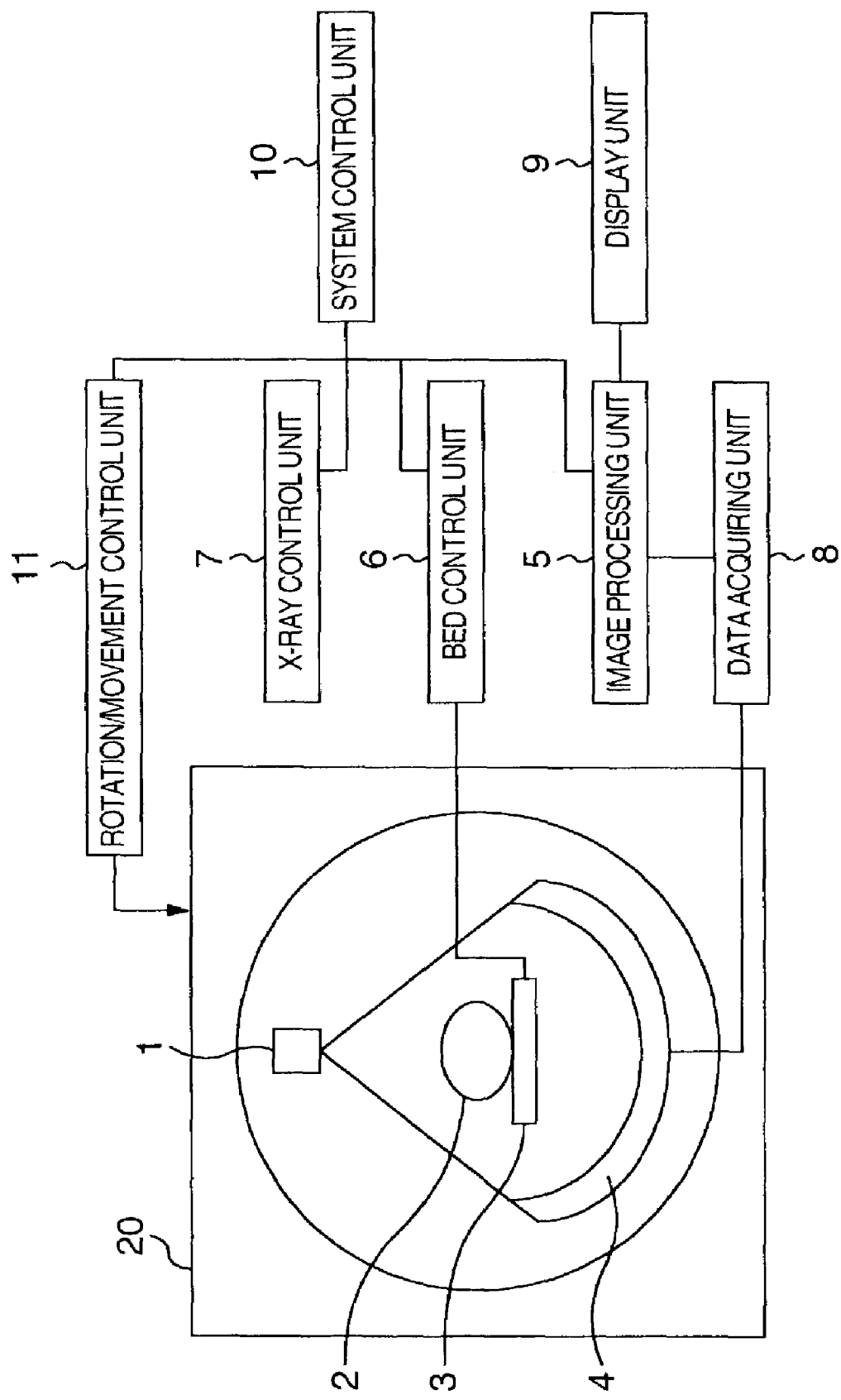
FIG. 1 is a structural diagram of an X-ray CT apparatus according to the present invention.

FIG. 1 is a block diagram for showing a structure of an X-ray CT apparatus according to the present invention.

In an X-ray CT apparatus 20, fan-beam X-rays (normally, being obtained via a collimator from X-ray source, will be referred to as an "X-ray source" containing this collimator) are irradiated from an X10 ray source 1 onto an object 2 to be examined located on a bed 3, and then, an amount of X-rays which have penetrated through the object 2 is detected by an X-ray detector 4 which is arranged in a fan shape and positioned opposite to the X-ray source 1. While both the X-ray source 1 and the X-ray detector 4 are rotated around the object 2 in a constant time period, a data acquiring unit 8 acquires an X-ray transmission amount data which is detected by the X-ray detector 4. With respect to this acquired data, a tomographic image is reconstructed by an image processing unit 5, and the reconstructed tomographic image is displayed on a display unit 9. Also, while the tomographic image data is stored into a memory, the stored tomographic image data is utilized in a post processing operation and also a display purpose. The X-ray detector 4 may be realized by multi channel type X-ray detector of either single column type (single slice) or plural column type (multi-slice).

An X-ray control unit 7 controls an amount of X-rays irradiated from the X-ray source 1, and a bed control unit 6 moves/controls the bed 3 along a body axial direction. A rotation/movement control unit 11 performs both a rotation control of the X-ray source 1 and the X-ray detector 4 located opposite to the X-ray source 1, and a movement control of a gantry unit which accomodates thereinto both the X-ray source 1 and the X-ray detector 4. A system control unit 10 controls the X-ray control unit 7, the bed control unit 6, the image processing unit 5, and the rotation/movement control unit 11.

FIG. 2 is an explanatory diagram for representing both a measuring operation executed on a body axis of the object 2 and a movement of the object 2 along a body axial direction in the case that both the X-ray source 1 and the X-ray detector 4 shown in FIG. 1 are operated, while the X-ray source 1 is located opposite to the X-ray detector 4. It should be noted that a direction perpendicular to this paper plane corresponds to a fan-shaped portion of an X-ray beam, and a direction of an arrow "A" corresponds to the body axial direction. The X-ray detector 4 is arranged in a fan shape along the direction perpendicular to the paper plane. It should also be noted an effective detection width where X-rays actually impinge on a plane of the X-ray detector 4 is defined as a "W."

Both the X-ray source 1 and the X-ray detector 4 own both such an operation that the X-ray source 1 and the X-ray detector 4 are rotated with respect to the object 2, and also another operation that the X-ray source 1 and the X-ray detector 4 are relatively moved along the body axial direction indicated by the arrow "A" in this drawing. In this case, the relative movement implies such a case that the bed 3 is moved, or such a case that both the X-ray source 1 and the X-ray detector 4 are moved instead of the bed 3. The following operations are explained by way of the latter case.

In accordance with the present invention, both the X-ray source 1 and the X-ray detector 4 are rotated by 1 turn at a certain position on the body axis so as to execute a CT measurement, while the X-ray source 1 is located opposite to the X-ray detector 4. The movement of both the X-ray source 1 and the X-ray detector 4 is controlled in such a manner that both the X-ray source 1 and the X-ray detector 4 are moved over a predetermined distance "L" along the body axial direction after this CT measurement has been carried out by this one rotation. This moving control is executed by the rotation/movement control unit 11. At a position on the body axis after the X-ray source 1 and the X-ray detector 4 have been moved over the predetermined distance "L", both the X-ray source 1 and the X-ray detector 4 are again rotated so as to execute a CT measurement, while the X-ray source 1 is located opposite to the X-ray detector 4. Subsequently, while the X-ray source 1 and the X-ray detector 4 are moved in a continuous step manner by the distance "L", CT measurements are repeatedly carried out. This moving amount "L" is smaller than an X-ray incident plane, and is equal to a target slice width of a tomographic image according to the present invention. In FIG. 2, a position "$P_2$" of the X-ray source 1 when this X-ray source 1 is moved by a distance "L" (L=W/2) is also displayed with respect to an original position "$P_1$" of the X-ray source 1. These positions "$P_1$" and "$P_2$" correspond to such position capable of specifying the X-ray source, for example, a center position and an edge position of the X-ray source 1.

FIG. 3 indicates such a case that at a certain angle (indicated by projection (view) angle "j") while both the X-ray source 1 and the X-ray detector 4 are rotated by 360 degrees, a measurement value of a slice width of W/2 is obtained by way of a calculation. FIG. 3 is a diagram for indicating both a CT measurement value "$b_k$" in the case that an effective detector width of an incident X-ray is "W" and a moving distance "L" is set to L=W/2, and also a measurement value "$a_k$" at a slice width W/2 to be obtained, while the CT measurement value "$b_k$" expresses an output of the X-ray detector 4, or such an output obtained by processing the output of the X-ray detector 4 based upon various sorts of pre-processing operations (namely, various sorts of corrections, and logarithm conversions). In this drawing, symbols "$b_0$", "$b_1$", "$b_2$", "$b_3$", - - - , are given as follows:

"$b_0$" - - - A CT measurement value at a starting position "$S_0$" on the body axis;

"$b_1$" - - - A CT measurement value at a position "$S_1$" separated from the starting position "$S_0$" by 1 pitch;

"$b_2$" - - - A CT measurement value at a position "$S_2$" separated from the position "$S_1$" by 1 pitch;

"$b_3$" - - - A CT measurement value at a position "$S_3$" separated from the position "$S_2$" by 1 pitch;

In this case, the CT measurement values "$b_0$", "$b_1$", "$b_2$", "$b_3$", - - - , correspond to such values that channel numbers "i" and projection (view) angles "j" are employed as a factor. For example, if a CT measurement value is "$b_n$", then this CT measurement value is equal to $b_n$ (i, j). The projection angles "j" are the respective values within such a range of j=0° to 360°, 0° to 180°, and 0° to 180°+β.

These CT measurement values "$b_0$", "$b_1$", "$b_2$", "$b_3$", - - - , are expressed by being discriminated from "$b_0$", "$b_2$", - - - , $b_1$, $b_3$, - - - , in FIG. 3(i) and FIG. 3(ii).

On the other hand, assuming now that measurement values at the slice width W/2 are defined as "$a_0$", "$a_1$", "$a_2$", "$a_3$", - - - , as shown in FIG. 3(iii), with respect to each of areas "$R_1$", "$R_2$", "$R_3$", - - - , the below-mentioned relationship may be established. Since the above-described measurement values at the slice width W/2 are obtained by way of a calculation, these measurement values are defined as "virtual measurement values." The areas $R_1$, $R_2$, $R_3$, - - - , are defined from the starting position "$S_0$" on the body axis in the order of W/2. It should be understood that these areas $R_1$, $R_2$, $R_3$, - - - , may have such a relationship that these areas are sequentially located adjacent to each other.

$$b_0 = a_0 + a_1$$

$$b_n = a_n + a_{n+1} \text{ (note: } n \geq 1)\qquad \text{formula 1}$$

If the formula 1 is generalized, when W/N, then the generalized formula is given as follows:

$$b_n = \sum_{i=0}^{N-1} a_{n+1} \ (n \geq 0)$$

In this case, symbol "$a_0$" corresponds to a virtual measurement value in the first area "$R_1$". When another virtual measurement value of "$a_n$" is obtained, it becomes the following formula 2:

$$a_{n+1} = b_n - a_n \ (n \geq 0)$$

$$a_n = b_{n-1} - a_{n-1} \ (n \geq 1) \qquad \text{formula 2}$$

The following fact can be revealed from the formula 2. That is, symbols "$b_0$" and "$b_n$" correspond to the CT measurement values, and are known. If the virtual measurement value "$a_0$" is known, then all of "$a_n$ ($n \geq 1$)" can be obtained by utilizing the formula 2. As apparent from FIG. 3(iii), "$a_n$ ($n \geq 1$)" may be regarded as a CT measurement value at a slice width of W/2. Since this "$a_n$ ($n \geq 1$)" is used to perform the reconstruction, a plurality of reconstructed images having the slice width of W/2, which are sequentially located adjacent to each other, can be obtained. As a consequence, resolution along the body axial direction may be improved. In this case, each of "$a_n$ ($n \geq 1$)" corresponds to such a value that a channel number "i" and a projection (view) angle "j" are factors, and is given as $a_n$(i, j). The projection angle "j" corresponds to each value within ranges of j=0° to 360°, 0° to 180°, and 0° to 180°+β. The reconstruction of $a_n$($n \geq 0$) is given as follows:

Reconstruction of W/2 slice width in area $R_1$ is carried out by employing $a_0$(i, j).

Reconstruction of W/2 slice width in area $R_2$ is carried out by using $a_1$(i, j).

Reconstruction of W/2 slice width in area $R_3$ is carried out by employing $a_2$(i, j).

"$a_n$($n \geq 1$)" is such a value which is obtained under such an initial condition that "$a_0$" is obtained.

Various sorts of setting examples of "$a_0$" will now be explained as follows:

(i) $a_0 = a_1$. In other words, an example is set by that $a_0 = b_0/2$.

This example becomes effective in such a case that no object under examination is present at the X-ray incident position of the starting position "$S_0$."

(ii) An example is set by that "$a_0$" is obtained from a linear interpolation of $a_n$($n \geq 1$).

For example, in the case of two-point interpolation, there is such a relationship:

$$a_1 = (a_0 + a_2)/2 \qquad \text{formula 3.}$$

Accordingly, "$a_0$" is given as follows:

$$a_0 = 2a_1 - a_2$$

$$= 2(b_0 - a_0) - (b_1 - b_0 + a_0)$$

$$= 3b_0 - b_1 - 3a_0 \qquad \text{formula 4}$$

Therefore, "$a_0$" is defined as follows:

$$a_0 = (3b_0 - b_1)/4 \qquad \text{formula 5}$$

As a consequence, "$a_0$" is identical to the interpolation result obtained from "$b_0$" and "$b_1$".

(iii) An example of calculating "$a_0$" which may minimize $D = \Sigma(a_{n+1} - a_n)^2$.

An error of the value of "$a_0$" appears in $(a_{n+1} - a_n)$. From this characteristic, "$a_0$" capable of minimizing "D" may be employed. That is to say, the below-mentioned formula may be obtained:

$$\begin{aligned} a_{n+1} &= b_n - a_n \qquad \text{formula 6}\\ &= b_n - (b_{n-1} - a_{n-1})\\ &= b_n - (b_{n-1} - (b_{n-2} - a_{n-2}))\\ &= b_n - (b_{n-1} - (b_{n-2} - (b_{n-3} - a_{n-3})))\\ &= b_n - b_{n-1} + b_{n-2} - b_{n-3} + - \ldots (-1)^n a_0\\ &= \sum_{k=0}^{n} (-1)^k b_{n-k} - (-1)^n a_0 \end{aligned}$$

$$D = \Sigma(a_{n+1} - a_n)^2 \qquad \text{formula 7.}$$

If the formula 6 is substituted for the formula 7 to cancel "$a_n$", then "D" becomes a function of "$b_n$" and "$a_0$". Since "$b_n$" corresponds to the measurement value and is known, "$a_0$" capable of minimizing "D" may be obtained.

In the above-described embodiment mode, the slice width to be obtained is selected to be W/2. The present invention may be applied to another example of slice widths of W/3 and W/4. FIG. 4A and FIG. 5A show explanatory diagrams of this example. In the example of FIG. 4A (slice width of W/3), both the X-ray source 1 and the X-ray detector 4 located opposite to the X-ray source 1 are moved in a pitch of W/3, and further, both the X-ray source 1 and the X-ray detector 4 are rotated by 1 turn at each of pitch stopping points so as to perform a CT measurement. As a result, a virtual measurement value "$a_n$" of the slice width (W/3) may be obtained. Also, CT measurement values of "$b_0$", "$b_3$", "$b_6$" - - - , are shown in FIG. 4(i), "$b_1$", "$b_4$", "$b_7$" - - - , are shown in FIG. 4A(ii), and CT measurement values "$b_2$", "$b_5$", "$b_8$", - - - , are indicated in FIG. 4A(iii). In this case, a relationship between "a" and "b" is given as follows:

$$b_n = a_n + a_{n+1} + a_{n+2} \ (n \geq 0) \qquad \text{formula 8}$$

In the case of two-point interpolation, the following formula 9 is given:

$$a_1 = (a_0 + a_2)/2$$

$$a_2 = (a_1 + a_3)/2 \qquad \text{formula 9}$$

Similar to the above-described case, since the virtual measurement values "$a_0$" and "$a_1$" are calculated from the formula 9, the virtual measurement value $a_n$ ($n \geq 0$) may be obtained.

It should also be noted that both "$b_n$" and "$a_n$" are realized by employing the two factors of the channel number "i" and the projection angle "j."

FIG. 5A shows an example of the slice width of W/4. That is, both the X-ray source 1 and the X-ray detector 4 are moved at a pitch of W/4, and a CT measurement of 360 is carried out each of the pitch stopping points. Both "a" and "b" may establish the below-mentioned relationship.

$$b_n = a_n + a_{n+1} + a_{n+2} + a_{n+3} \ (n \geq 0) \qquad \text{formula 10}$$

$$a_1 = (a_0 + a_2)/2$$

$$a_2 = (a_1 + a_3)/2$$

$$a_3 = (a_2 + a_4)/2 \qquad \text{formula 11}$$

Since the virtual measurement values "$a_0$", "$a_1$", "$a_2$" are calculated from formulae 10 and 11, "$a_n (n \geq 3)$" may be obtained. A reconstruction of a W/N slice width is carried out by using $a_n(i, j)$.

The example of the slice width of W/3 shown in FIG. 4A may be expanded to another example of a slice width of "2W/3" indicated in FIG. 4B. In the slice width of (2W/3), virtual measurement values of "$c_0$", "$c_1$", "$c_2$", are defined by the below-mentioned relationship:

$$C_n = a_{2n} + a_{2n+1} \ (n \geq 0) \qquad \text{formula 12}$$

The example of the slice width W/4 shown in FIG. 5A may be expanded to another example of a width "3W/4" denoted in FIG. 6B. Assuming now that a virtual measurement value at the slice width of (3W/4) is equal to "$C_n$", this virtual measurement value "$C_n$" is defined as follows:

$$C_n = a_{3n} + a_{3n+1} + a_{3n+2} \qquad \text{formula 13}$$

When this formula (13) is generalized, the below-mentioned formula (14) is given as follows:

$$C_n = \sum_{i=0}^{M-1} a_{Mn+i} \ (n \geq 0)$$

It should also be noted that a measurement of such a slice width of (M×W)/N (both M and N being integers) may be commonly carried out, while a measurement at a slice width of W/N is performed as a basic measurement, and an image is reconstructed by employing $C_n(i, j)$. The above-described formuale 1 to 14 may be established every factors of "i" and "j."

The above-explained embodiment mode is directed to such a sequential operation of CT measurement→movement→CT measurement movement, - - - . Alternatively, there is another method of a helical scanning system in which while both the X-ray source and the X-ray detector are moved, a CT measurement is carried out. For example, in the example of the slice width of (W/2), both the X-ray source 1 and the X-ray detector 4 are moved by a pitch of W/2. During this moving time duration, both the X-ray source 1 and the X-ray detector 4 are rotated by 1 turn so as to perform a CT measurement. Next, both the X-ray source 1 and the X-ray detector 4 are moved by a pitch of W/2. During this moving time duration, both the X-ray source 1 and the X-ray detector 4 are similar rotated by 1 turn so as to perform a CT measurement. Even when the above-explained helical scanning operation is carried out, such a CT measurement as shown in FIG. 3 may be carried out. As a result, virtual measurement values "$a_0$", "$a_1$", "$a_2$", - - - , may be obtained at each of the preselected angles, namely every factors "i" and "j". This technical idea may be similarly applied to other examples of other slice widths.

Another embodiment mode of the present invention will now be explained. This new embodiment mode is not such an example that one column of the X-ray detector is arranged along the slice width direction (FIG. 2), but corresponds to such an example that the present invention is applied to a multi-slice X-ray detector in which two, or more columns of X-ray detectors are arranged along the slice width direction. Assuming now that a total arranging number of X-ray detectors is selected to be "P", such a CT apparatus equipped with this multi-slice X-ray detector is featured by that "P" pieces of tomographic images can be acquired during one CT measurement. Moreover, each of these tomographic images corresponds to such a tomographic image made of a slice width "W" per an X-ray detector.

Under such a circumstance, in accordance with the present invention, even in such a multi-slice X-ray detector, it is possible to acquire a tomographic image having a slice width which is narrower than this slice width of W. FIG. 6 shows an example of a multi-slice X-ray detector 40, while "P" is equal to 2. The X-ray detector 40 is arranged by two sets of X-ray detector elements 41 and 42 having the same slice widths of "W." These two X-ray detector elements 41 and 42 correspond to multi-channel type X-ray detectors having a plurality of X-ray detector elements which are arranged in a fan shape along directions perpendicular to the paper plane, respectively. Since the X-ray detector 40 having these X-ray detectors 41 and 42 are rotated while being located opposite to the X-ray source 1, two sets of CT measurement values located adjacent to each other may be obtained from the X-ray detector elements 41 and 42 by rotating this X-ray detector 40 by 1 turn. Thus, two tomographic images in total may be acquired, namely, one tomographic image may be acquired in correspondence with the X-ray detector element 41, and also one tomographic image may be acquired in correspondence with the X-ray detector element 42.

With respect to the relevant multi-slice X-ray detector 40 of FIG. 6, rotation/movement thereof are controlled by the rotation/movement control unit 11. In this case, similar to the above-described embodiment mode of FIG. 2, tomographic images having various sorts of slice widths may be acquired. In particular, it can be avoided that the detector does not measure the same place by selecting the moving amount to be equal to PW/N (P<N and also, both P and N are relatively prime). A typical example will now be indicated as follows:

(i) An example of acquiring a tomographic image having a slice width of (W/3).

Figure 7:
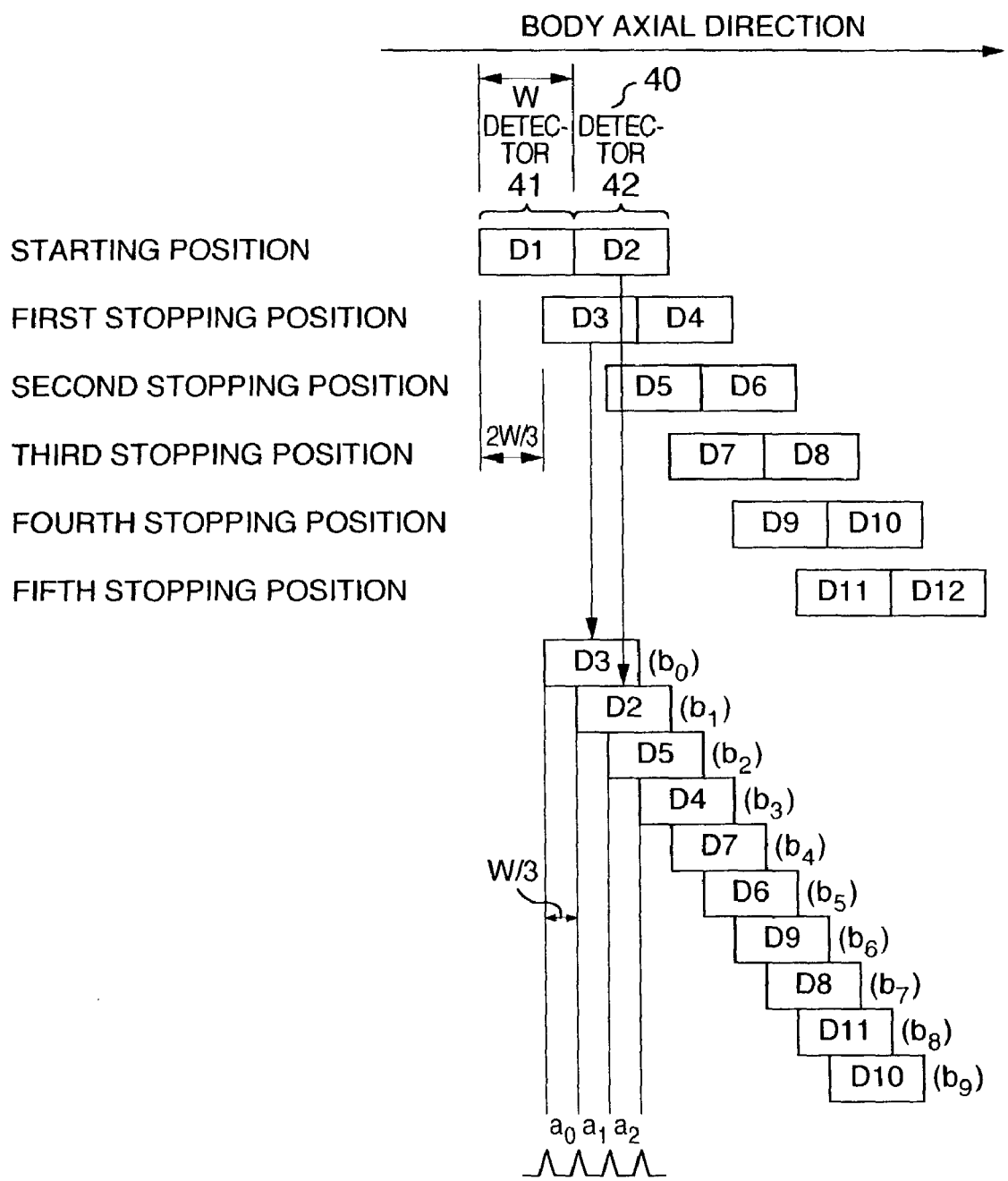
FIG. 7 is a diagram for indicating a multi-slice X-ray detector.

This example may be realized by that while both the X-ray source 1 and the X-ray detector 40 are moved in a pitch of (2W/3), both the X-ray source 1 and the X-ray detector 40 are rotated by 1 turn under opposite condition at each of stopping points (including starting point) so as to perform a CT measurement. FIG. 7 is a time chart for explaining this operation. In FIG. 7, such an example is indicated. That is, measurement data are derived in this order of D3, D2, D5, D4, D7, - - - , to be arranged in such a manner that a positional shift of these measurement data becomes W/3, so that CT measurement values $a_0$, $a_1$, $a_2$, - - - , of the slice width of (W/3) are acquired. The arranged measurement data D3, D2, D5, D4, - - - , correspond to $b_0$, $b_1$, $b_2$, $b_3$ - - - , shown in FIG. 2. Similar to FIG. 4A, such a reconstructed image with the slice width of W/3 may be acquired.

(ii) Other examples.

Similar to the first embodiment mode, CT measurement values having slice widths of W/N and MW/N may be obtained.

Figure 8:
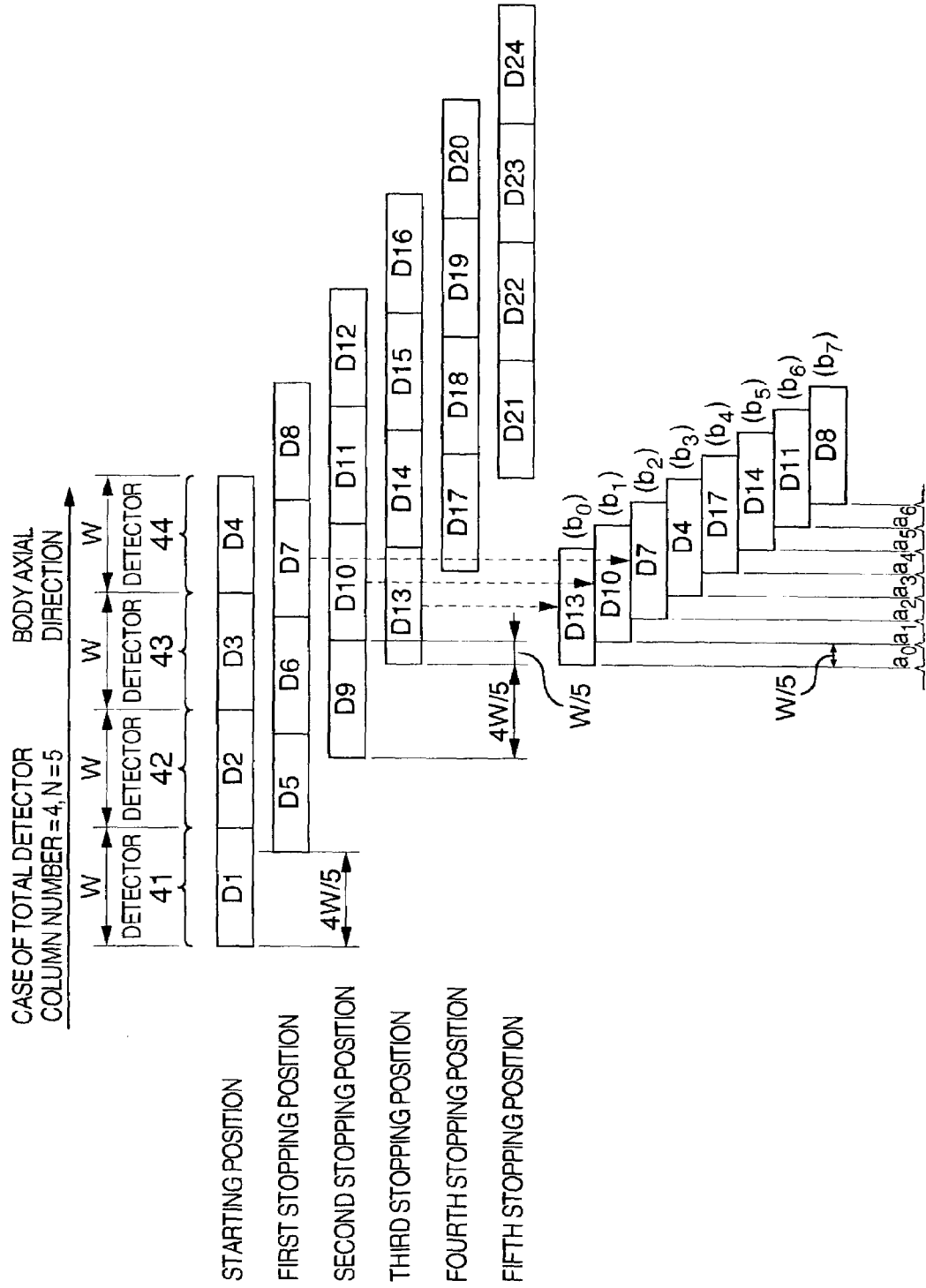
FIG. 8 is a diagram for indicating a multi-slice X-ray detector.

FIG. 8 shows an application example in which detectors 41 to 44 made of a total slice detector column number P=4 are employed. This is such an example that the slice width is selected to be W/5. This example may be realized by that while both the X-ray source 1 and the X-ray detector 40 are moved in a pitch of (4W/5), both the X-ray source 1 and the X-ray detector 40 are rotated by 1 turn at each of stopping points of 4W/5 so as to perform a CT measurement. Measurement data are derived in this order of D13, D10, D7, D4, - - -, to be arranged in such a manner that a positional shift of these measurement data becomes W/5, so that CT tomographic images having the slice width of (W/5) are acquired. The arranged measurement data D13, D10, D7, D4, - - -, correspond to $b_0$, $b_1$, $b_2$, $b_3$ - - -, shown in FIG. 2. While the formulae 10 and 11 are expanded to N=5, virtual measurement values $a_0$, $a_1$, $a_2$, - - -, are acquired. These virtual measurement values are employed to produce a reconstructed image.

Furthermore, similar to the first embodiment mode, there is another method. That is, it is moved by 1 pitch, these X-ray source and X-ray detector are rotated by 1 turn so as to execute a CT measurement. In any of the above-described cases, the measurement data are derived to be arranged (on calculation) in such a way that the positional shift of the measurement data becomes equal to W/N. As a result, a virtual measurement value "$a_0(n \geq 0)$" is obtained.

In the above-described embodiment modes, the relationships between the pitch moving widths and the slice widths merely constitute one example, and therefore, other various mutual relationships may be established. Various other relationships may be realized by merely changing the method for acquiring the virtual measurement values.

The reason why the slice width is variably narrowed is to improve the resolution along the body axial direction. Next, this resolution improvement will now be explained. When a slice width is made wide, there is such a drawback that an image are blurred. On the other hand, if the slice width is wide, then there is such a merit that an observation image of a large region may be obtained. When a slice width is made narrow, there are such merits that resolution of an image may be improved, and an image having good contrast may be obtained. For instance, the X-ray CT apparatus of the present invention is direction to such a case. That is, when an observation image of a small region is wanted to be acquired, a narrow slice width may be set. Moreover, there is a merit that the slice width may be simply set. Conversely, such data as to various slice widths may be obtained by way of the calculation. As a result, there is an advantage that the resolution along the body axial direction can be freely adjusted.

In this case, a slice width setting method realized in the present invention will now be simply explained. That is, a slice width may be set by employing a collimator. Alternatively, while such a collimator is not used, a slice width may be set by directly using a physical detection width of the X-ray detector 4, or 40. With respect to the slice width set in the above manner, such a slice width which is made narrower than this set slice width may be set by entering the slice value via a keyboard, or a mouse. A moving pitch width is automatically set in order to satisfy this input set value. The rotation/movement control unit 11 performs controls of the rotation/movement/measurement by using this automatically set moving pitch width.

Figure 9:
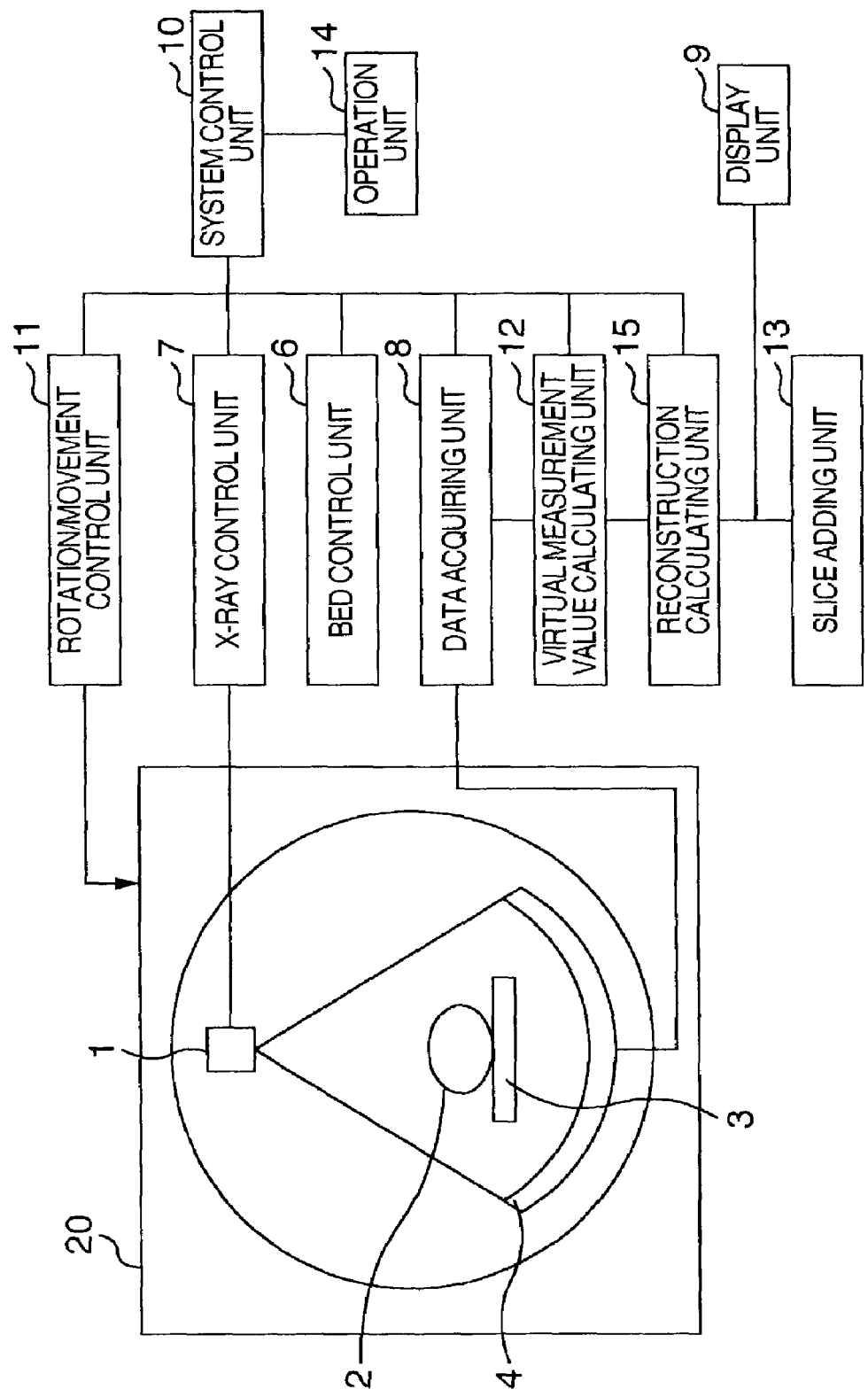
FIG. 9 is another structural diagram of an X-ray CT apparatus according to the present invention.

FIG. 9 is another structural diagram of an X-ray CT apparatus according to the present invention. In comparison with FIG. 1, this X-ray CT apparatus owns such a different structure, namely, an operation unit 14, a virtual measurement value calculating unit 12, a slice adding unit 13, and a reconstructing unit 15. The operation unit 14 is to instruct/input a CT measurement condition, a measurement portion, a measuring method, and so on. Although not shown in FIG. 1, this measurement unit 14 is originally provided in FIG. 1. The virtual measurement value calculating unit 12 corresponds to such a numeral value processing means for processing CT-measured data so as to convert the processed data into data having a desirable slice width. This virtual measurement calculating unit 12 corresponds to a very important element of the present invention. The above-explained conversion corresponds to such a process operation for converting "b" into "a", as viewed in FIG. 3. The slice adding unit 13 executes such a process operation in which the dimension of the slice width is made thick after the reconstruction has been carried out. For example, such a slice adding process operation is performed in such a manner that a slice width of W/2 is converted into a slice width of 3W/2.

Figure 10:
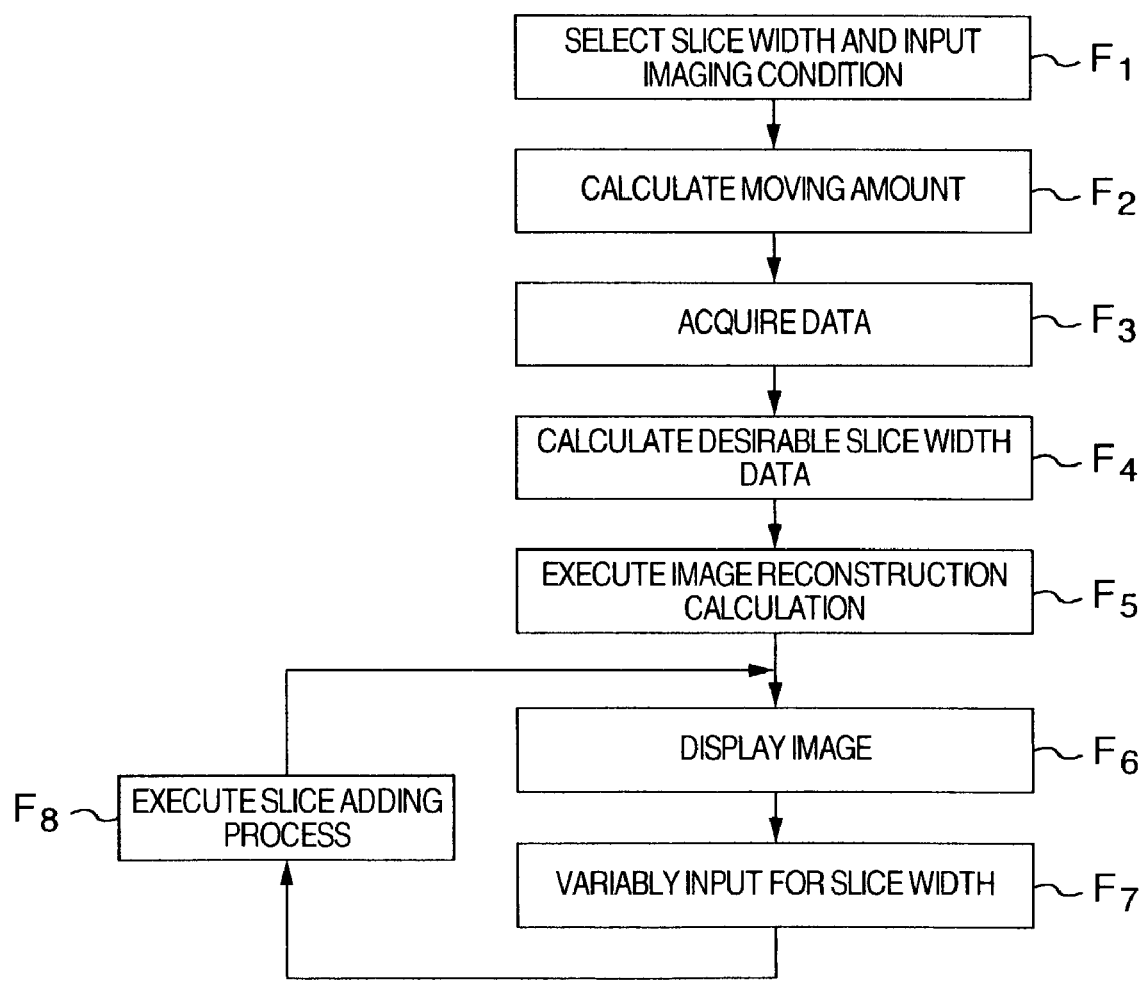
FIG. 10 is a flow chart for explaining an image processing operation executed by the X-ray CT apparatus of FIG. 9.

FIG. 10 shows a process flow operation of FIG. 9.

Both a slice width of a tomographic image and other imaging conditions are set by using the operation unit 14 to commence a measuring operation (flow $F_1$). Since the slice width may be made thick by the slice width adding process (flow $F_7$) after the image reconstructing process operation, the thinnest slice value among the required slice widths is selected. Furthermore, a moving pitch amount as to both the X-ray source 1 and the X-ray detector 4 is calculated, which corresponds to this thinnest slice width (flow $F_2$).

In the X-ray CT apparatus 20, the X-ray beams are irradiated from the X-ray source 1 onto the object 2 under examination located on the bed 3, and then, an amount of X-rays which have penetrated through the object 2 is detected by the X-ray detector 4 which is arranged in the fan shape with respect to the X-ray source 1. While both the X-ray source 1 and the X-ray detector 4 are rotated around the object 2 in a constant time period, the data acquiring unit 8 acquires X-ray transmission amount data which is detected by the X-ray detector 4 (flow $F_3$).

With respect to this data acquisition, the numeral process operation is performed by the virtual measurement value calculating unit 12 so as to convert the acquired X-ray amount data into desirable slice width data (flow $F_4$). With respect to this conversion data, a tomographic image is reconstructed by the reconstruction calculating unit 15 (flow $F_5$), and then, the reconstructed tomographic image is displayed on the display unit 9 (flow $F_6$). Furthermore, if an increase of this slice width is further requested (flow $F_7$), an adding process operation is carried out so as to enlarge the slice width (flow $F_8$).

Although the above-described embodiment modes have been described by using such an example of the third-generation CT apparatus, the present invention may be similarly applied to such a fourth-generation CT apparatus in which while X-ray image detectors are arranged over 360 degrees, only an X-ray source is rotated.

The invention claimed is:

1. An X-ray CT apparatus comprising:
    an X-ray source for irradiating a fan beam X-ray having a predetermined width;
    an X-ray detector which is arranged opposite to said X-ray source while sandwiching an object to be examined, and is rotated around said object in combination with said X-ray source under opposite-arranging condition;
    means for moving, plural times; any one of both said X-ray source and said X-ray detector located opposite to said X-ray source, and a bed on which said object is mounted at a predetermined pitch which is made narrower than an effective X-ray detection width "W" of the X-ray;

means for rotating both said X-ray source and said X-ray detector located opposite to said X-ray source so as to execute a CT measurement, and for acquiring a detection signal obtained from said X-ray detector;

virtual measurement value calculating means for calculating virtual detection data having a slice width M/N times the effective detection width "W" of the X-ray from said detection signal, while symbols "M" and "N" are integers, are defined by M<N, and are relatively prime; and means for reconstructing a tomographic image from said virtual detection data;

wherein a virtual detection data an for a CT measurement value $b_n$ for said effective X-ray detection width W is represented as $$b_n \sum_{i=0}^{N-1} a_{(n*N+i)} \quad (n \geq 0),$$

and a virtual detection data $a_0$ firstly calculated is obtained from any one of the equation of $a_0=b_0/N$, linear interpolation from an in the vicinity of the $a_0$ and a condition minimizing the equation of $DE=\Sigma(a_{n+1}-a_n)^2$.

2. An X-ray CT apparatus as claimed in claim 1 wherein:
said virtual measurement value calculating means includes a means for calculating virtual detection data having a slice width of "MW/N", which are sequentially located adjacent to each other, from said detection signal.

3. An X-ray CT apparatus as claimed in claim 1 wherein:
both said detection signal and said virtual detection data satisfy:
detection signal=N×(virtual detection data corresponding to area every pitch W/N along body axial direction of the object), with respect to each of rotation angles.

4. An X-ray CT apparatus as claimed in claim 1, wherein:
said means for acquiring the detection signal includes means for rotating both said X-ray source and said X-ray detector so as to perform a CT measurement, while either said X-ray source and said X-ray detector or said bed is moved in order to realize said predetermined pitch.

5. An X-ray CT apparatus as claimed in claim 1, wherein assuming that said predetermined pitch is PW/N, the slice width takes any one of W/N, 2W/N, . . . , (P−1)W/N as a virtual detection data, wherein P is an integer.

6. An X-ray CT apparatus comprising:
an X-ray source for irradiating a fan beam X-ray having a predetermined width;
an X-ray detector which is arranged opposite to said X-ray source while sandwiching an object to be examined on a bed, and is rotated around said object in combination with said X-ray source under opposite-arranging condition;

display means for displaying information for setting a moving distance L, when either a combination of said X-ray source and said X-ray detector or said bed is moved in a body axial direction of said object to be examined;

moving distance setting means for setting said moving distance L as PW/N for an effective detection width W of said X-ray detector on the basis of said information displayed, wherein N is an integer greater or equal to 2, P is defined as P<N, and P and N are relatively prime;

moving means for moving either said combination of said X-ray source and said X-ray detector or said bed according to said PW/N set in said body axial direction of said object to be examined;

signal acquiring means for executing CT measurement with said effective detection width W by rotating said X-ray source and said X-ray detector under a condition that either said combination of said X-ray source and said X-ray detector or said bed is moved by said moving means in said body axial direction of said object to be examined and for acquiring signals of transmission X-ray through said object to be examined from said X-ray detector as a CT measurement value "b";

virtual measurement value calculation means for calculating a virtual measurement value "a" of W/N for said effective detection width W of said X-ray detector on the basis of said CT measurement value "b" acquired by said signal acquiring means, said moving distance L set by said moving distance setting means and a starting position $S_0$ of said CT measurement value "b" acquired by said signal acquiring means; and means for reconstructing a tomographic image of said object to be examined having a slice width of PW/N for said effective detection width of said X-ray detector on the basis of said calculated virtual measurement value "a".

7. The X-ray CT apparatus according to claim 6, wherein said display means comprises means for displaying a position $P_1$ of said X-ray source before movement and a position $P_2$ of said X-ray source after movement.

8. The X-ray CT apparatus according to claim 6, wherein said virtual measurement value calculation means comprises means for obtaining said virtual measurement value "a" on the basis of a condition selected among a first condition that the virtual measurement value "a" is obtained as Pb/N, when no object to be examined is present at an X-ray incident position of said starting position $S_0$ of measurement of said object to be examined, a second condition that the virtual measurement value "a" is obtained by a linear interpolation between virtual measurement values having adjacent positional relationships to said virtual measurement value "a" to be obtained and a third condition that said virtual measurement value "a" is obtained so as to minimize a value obtained by applying a least-square method to a difference of virtual measurement values having adjacent positional relationships to said virtual measurement value "a" to be obtained.

* * * * *